US006178246B1

(12) United States Patent
Bebesel et al.

(10) Patent No.: US 6,178,246 B1
(45) Date of Patent: Jan. 23, 2001

(54) APPARATUS FOR THE ACTIVE SUPPRESSION OF NOISE RADIATED BY A SURFACE

(75) Inventors: Marius Bebesel, Munich; Rudolf Maier, Miesbach; Klaus Schmidts, Munich, all of (DE)

(73) Assignee: DaimlerChrysler AG, Stuttgart (DE)

( * ) Notice: Under 35 U.S.C. 154(b), the term of this patent shall be extended for 0 days.

(21) Appl. No.: 09/315,770

(22) Filed: May 20, 1999

(30) Foreign Application Priority Data

May 20, 1998 (DE) ........................................... 198 22 582

(51) Int. Cl.[7] ................................................. A61F 11/06
(52) U.S. Cl. ...................................... 381/71.2; 381/71.11
(58) Field of Search ................................ 381/71.2, 71.4, 381/71.8, 71.1, 71.3, 71.5, 71.6, 71.7, 71.9; 181/206, 207

(56) References Cited

U.S. PATENT DOCUMENTS 4,495,434 * 1/1985 Diepers et al. ..................... 310/338
5,115,472 * 5/1992 Park et al. .......................... 381/152
5,410,607 * 4/1995 Mason et al. ...................... 381/71.4
5,651,072 * 7/1997 Nakao et al. ...................... 381/71.2
5,812,684 * 9/1998 Steven ................................ 3891/86
6,031,917 * 2/2000 Mathur ............................ 381/71.11

FOREIGN PATENT DOCUMENTS 3834853 4/1990 (DE) .

OTHER PUBLICATIONS

The Journal of the Acoustical Society of America; vol. 98, No. 4, Oct. 1995, pp. 2174 to 2186.

* cited by examiner

*Primary Examiner*—Forester W. Isen
*Assistant Examiner*—Brian Tyrone Pendleton
(74) *Attorney, Agent, or Firm*—W. F. Fasse; W. G. Fasse

(57) ABSTRACT

Noise generated by a noise radiating surface is actively suppressed by at least two axially sensitive noise sensors which produce a control signal for controlling a noise suppression actuator. The sensors integrate the sensed signal in an axially selective manner. The at least two sensors are sensing the signal in two directions which preferably cross each other orthogonally. The control signal activates the actuator in such a way that the actuator counteracts deflections or vibrations of the noise generating surface such as a vehicle body wall.

15 Claims, 4 Drawing Sheets

APPARATUS FOR THE ACTIVE SUPPRESSION OF NOISE RADIATED BY A SURFACE

PRIORITY CLAIM

This application is based on and claims the priority under 35 U.S.C. §119 of German Patent Application 198 22 582.2, filed on May 20, 1998, the entire disclosure of which is incorporated herein by reference.

FIELD OF THE INVENTION

The invention relates to an active noise suppression of noise generated by a surface. At least one sensor such as a velocity sensor is connected to the noise radiating surface for providing a control signal that operates or controls an actuator that is effective on the surface to counteract the noise radiation.

BACKGROUND INFORMATION

Such a system is described, for example, in an article entitled "Active Control of Sound Radiation Using Volume Velocity Cancellation" by M. E. Johnson and S. J. Elliott, published in the "Journal of the Acoustic Society of America", Vol. 98(4), October 1995. A velocity sensor is used which covers the entire surface that radiates the noise, just as the actuator for suppressing the noise also covers the entire surface. The velocity sensor measures only the uneven numbered vibration modes especially the base mode (1,1). The actuator only counteracts these base mode vibrations. If the noise radiating surface oscillates at higher vibration modes which have only one vibration component which is even numbered, for example (1,2)-, (2,3)-, etc., then such a integrating surface sensor no longer provides an output signal, because the integration of overall vibration or oscillation peaks and valleys yields a sum signal=0. However, it has been-noted, that the degree of radiation at such vibration modes of a vibrating or oscillating plate increases as the excitation frequency increases. These vibration modes include at least one uneven numbered component, for example (1,2)-; (1,3)-; (2,3)-; (3,3)-; etc. modes.

OBJECTS OF THE INVENTION

In view of the foregoing it is the aim of the invention to achieve the following objects singly or in combination:

to provide an apparatus for the active noise suppression capable of sensing and suppressing vibration or oscillation modes having at least one uneven numbered component;

to use sensor distribution patterns on the surface of a vibrating plate so that the desired active counteracting noise suppression is achieved; and to use integrating sensors especially velocity sensors that have an axial sensitivity.

SUMMARY OF THE INVENTION

According to the invention an active noise suppression is achieved by controlling a noise suppressing actuator, that is effective on the noise generating surface, with a control signal generated by integrating sensors having an axial sensing selectivity, so that oscillations or vibrations are sensed in at least two directions crossing each other, preferably at a right angle in the (x, y) directions of a rectangular coordinate system.

Contrary to the prior art, the invention uses integrating sensors that are axially selective. Such sensors are preferably velocity sensors, or acceleration sensors, or deformation pick-ups, which are formed for example as piezo-film strips. As soon as a vibration mode having an uneven numbered component occurs along an axis of a surface covered with such a sensor the integrated sum signal provided by the sensor is no longer zero. As a result, the actuator controlled by the sensor signal can counteract the respective vibration mode of the plate. The arrangement of the sensors used according to the invention may assume various patterns described in more detail below, especially a rectangular coordinate matrix pattern.

BRIEF DESCRIPTION OF THE DRAWINGS

In order that the invention may be clearly understood it will now be described in connection with example embodiments, with reference to the accompanying drawings, wherein.

DETAILED DESCRIPTION OF PREFERRED EXAMPLE EMBODIMENTS AND OF THE BEST MODE OF THE INVENTION

Figure 1:
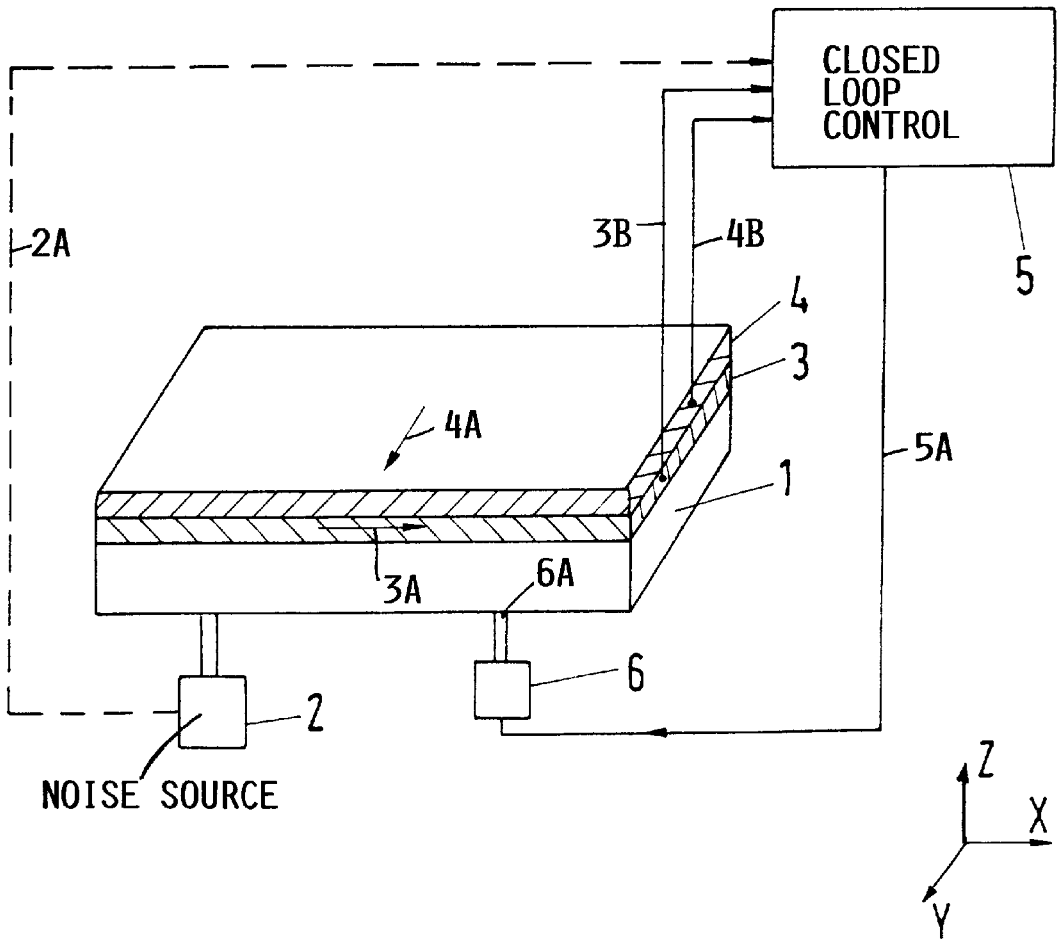
FIG. 1 shows one embodiment of an active plate noise suppressor having two velocity sensors each having an axially selective sensitivity to provide inputs to a closed loop control.

FIG. 1 shows an example embodiment with a noise radiating or generating component such as a plate 1 which may, for example be a structural component such as a vehicle body wall having a surface. A source of noise 2, such as an internal combustion engine of the vehicle, excites the plate 1 to cause the plate 1 to vibrate or oscillate. Two piezoelectric films 3 and 4 are secured to the plate 1 as signal integrating sensors. These piezo-sensor films 3 and 4 are directionally sensitive as indicated by the arrow 3A for the film 3 and by the arrow 4A for the film 4. Preferably, the directional sensitivities as indicated by the arrows 3A and 4A extend orthogonally to each other.

The piezoelectric films 3 and 4 are made, for example of stretched PVDF (polyvinylidene fluoride). These films have unidirectional, piezoelectric characteristics due to their stretching when these films are conventionally produced. The two films are arranged one on top of the other so that the preferred piezoelectric sensitivities as represented by the arrows 3A and 4A are positioned in parallel to the plane defined by the plate 1 but perpendicularly to each other. More specifically, the film 3 is sensitive to plate surface deflections in the x-direction and the film 4 is sensitive for respective plate surface deflections in the y-direction of a three-dimensional x, y, z-coordinate system shown in the lower-right corner of FIG. 1.

The sensed voltage signals produced by the sensor films 3 and 4 are supplied through conductors 3B and 4B to a closed loop feedback controller 5 which processes the sensed signals and provides a control signal on its feedback conductor 5A connected to an actuator 6 for exciting the plate 1 to counteract any noise vibrations of the plate 1. The actuator 6 may be physically connected to the plate 1 either at a point 6A as shown in FIG. 1 or on a surface area. In either instance the connection must be such that an effective active excitation power transmission into the plate is accomplished for counteracting vibration deflections of the plate 1.

FIG. 1 further shows a dashed line connection 2A between the noise source 2 and a respective input of the closed loop control 5. A sensor connected to the noise source 2 provides a feed-forward control signal through the conductor 2A to the closed loop control 5.

Due to the axially selective integrating effect of the two film sensors 3 and 4 the base vibration mode and other modes of the vibrating plate 1 are sensed. Such other modes have an uneven mode number either in the x-direction or in the y-direction. The sum signal is zero only for vibration modes with an even number in the respective direction to which the respective film 3 or 4 is allocated.

Figure 2:
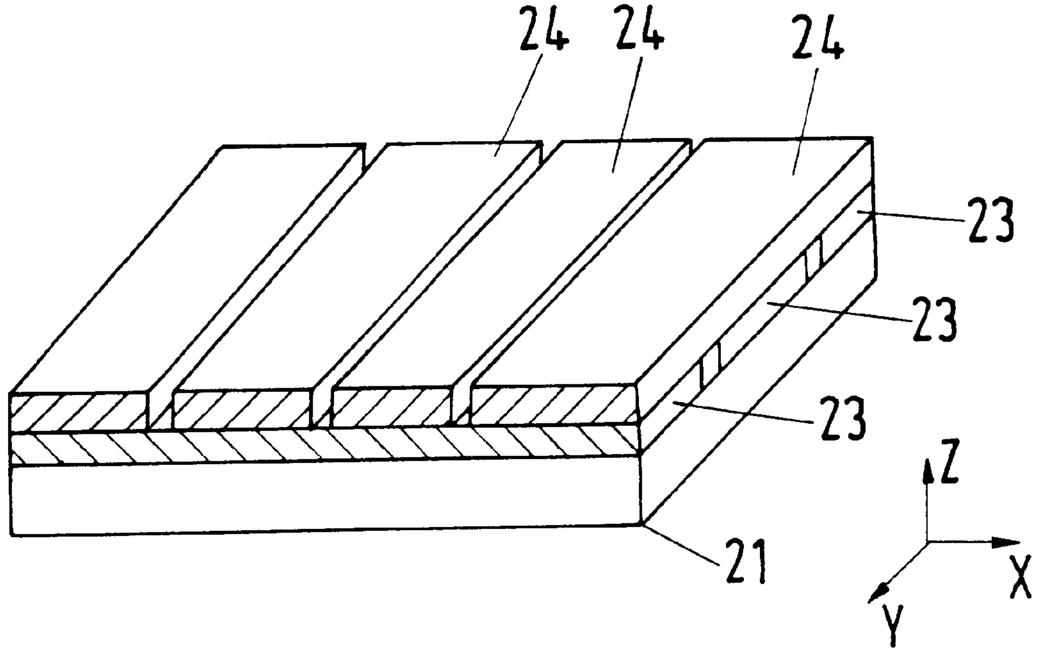
FIG. 2 illustrates the arrangement of strip shaped, axially selective sensors arranged in a crossover pattern on a plate that generates the noise to be suppressed.

FIG. 2 shows that instead of using large surface PVDF-films as directional sensors, it is possible to use strip shaped films functioning as axially selective integrating sensors. Strip-shaped sensors have the advantage that they are easily secured, for example by an adhesive even to the surface of curved plates without any problems. A plate 21 has secured to one of its flat surfaces film strips 23 forming piezoelectric sensors extending in the x-direction. Further, film strip sensors 24 are secured to the outer surface of the film strip sensors 23. The sensors 24 extend in the y-direction. These sensor strips 23 and 24 sense the velocity of plate oscillations or vibrations in the respective x- and y-directions and provide respective integrated signals to the controller 5 shown in FIG. 1. For this purpose all strip sensors 23 are electrically interconnected with each other. Similarly, all strip sensors 24 are electrically interconnected with each other for the respective signal integration. As a result, the sensed signal conductors leading from the interconnected strips 23 or 24 to the respective controller inputs provide summation signals representing the noise to be suppressed in the respective direction x or y.

Figure 3:
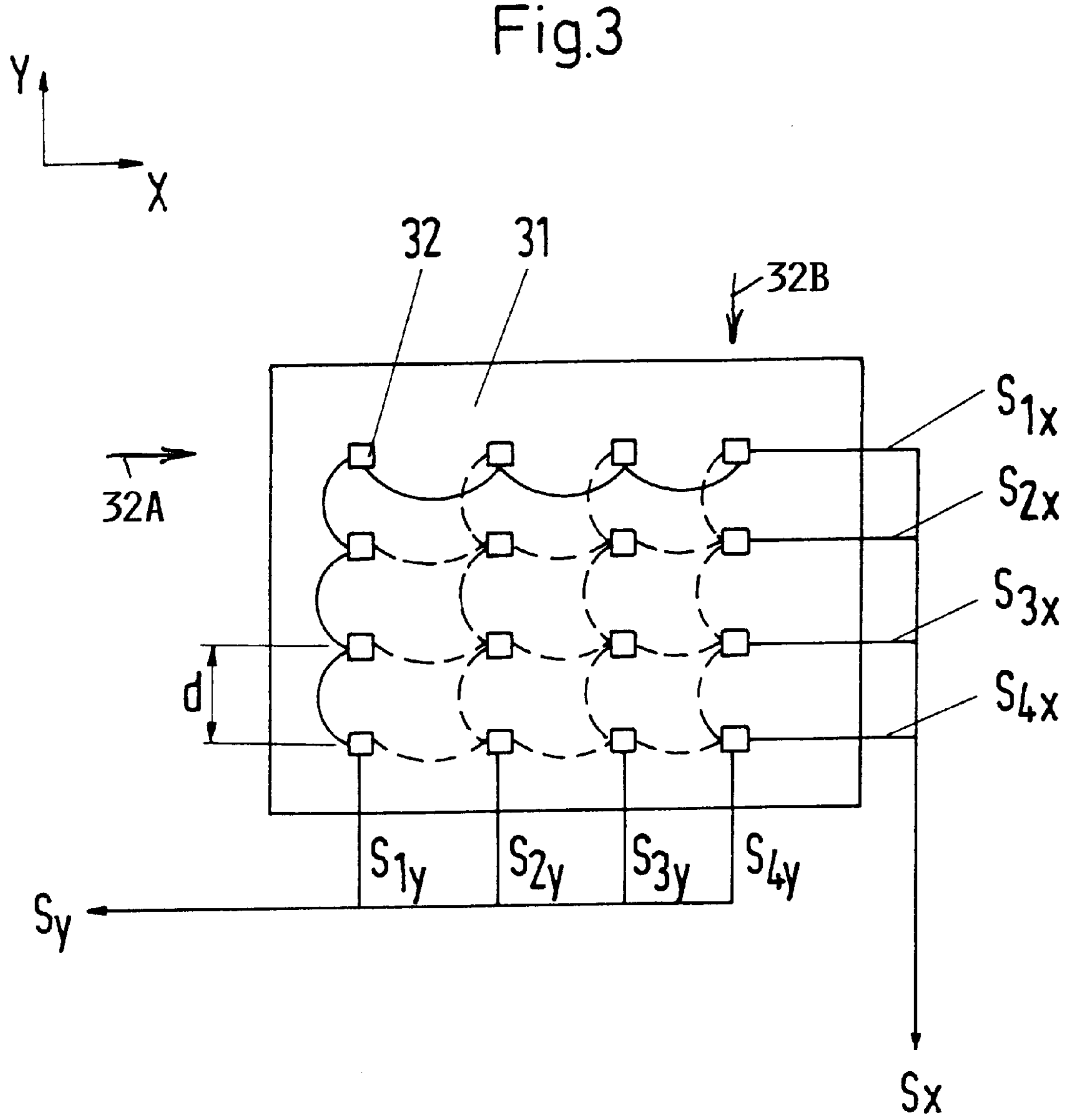
FIG. 3 shows the arrangement of velocity sensors in a row and column matrix pattern.

FIG. 3 shows an embodiment wherein the vibration velocity of a plate 31 is sensed by sensors 32 which are point sensors arranged in a matrix pattern in rows 32A and columns 32B. The rows 32A extend in the x-direction. The columns 32B extend in the y-direction. The sensors 32 are acceleration sensors secured to the surface of the plate 31 for example by an adhesive. The sensors of the rows 32A are electrically interconnected by row conductors S1x, S2x, S3x, S4x which are in turn interconnected by a further row conductor Sx providing respective summed row signals. Correspondingly, the sensors of the columns 32B are electrically interconnected by column conductors S1y, S2y, S3y, S4y connected in common to a further column conductor Sy providing respective summed column signals. The signals provided by the row conductor Sx and by the column conductor Sy provide information whether on the plate 31 vibrations modes occurred that altogether have a noise radiating effect. This is possible because the various sensed and integrated velocity values with positive or negative signs either cancel each other if they are of equal amplitude but opposite signs or they provide a difference signal as a summed or integrated control signal for the actuator 6 if the amplitudes differ.

It is necessary to adapt the spacing d between neighboring rows 32A and a respective spacing between neighboring columns 32B of the measuring grid structure formed by the acceleration sensors 32, to the respective plate structure and to the frequency range in which a noise reduction is required. In order to effectively reduce noise even for noise radiating structures having the highest possible vibration modes, the spacing d should be smaller than one quarter of the structure wavelength λ of the highest vibration mode of the respective noise generating structure ($d<\lambda/4$).

Instead of using acceleration sensors 32 as shown in FIG. 3, it is possible to use small dimension strain gages, piezoceramic sensors and piezo-films of suitably small dimensions.

Figure 4A:
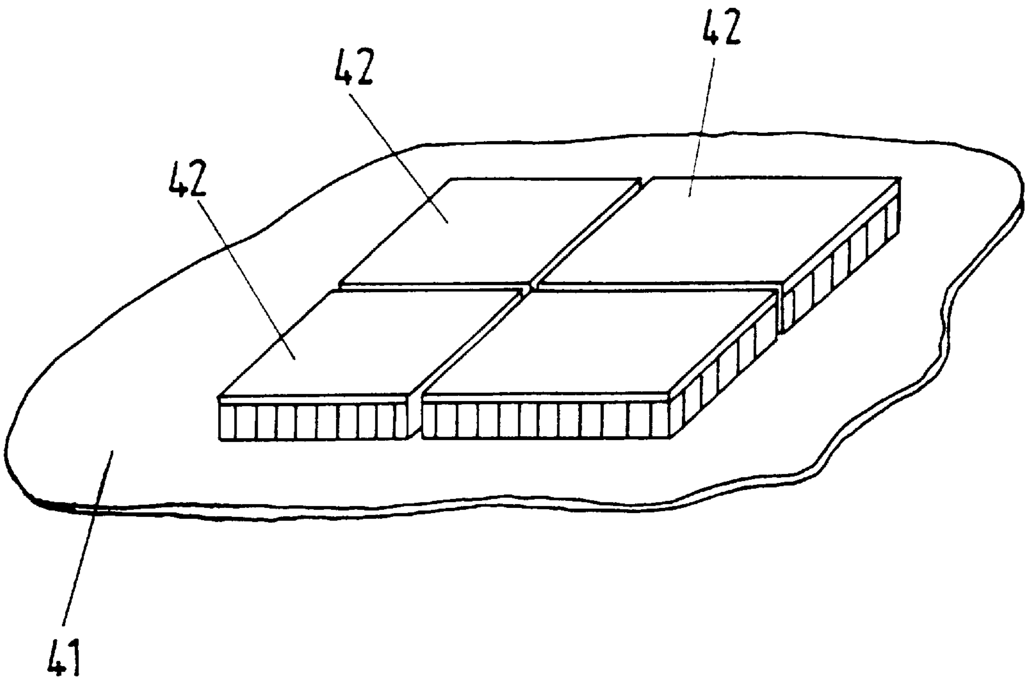
FIG. 4A is a perspective view of noise suppressing box elements distributed on the surface of a plate.
Figure 4B:
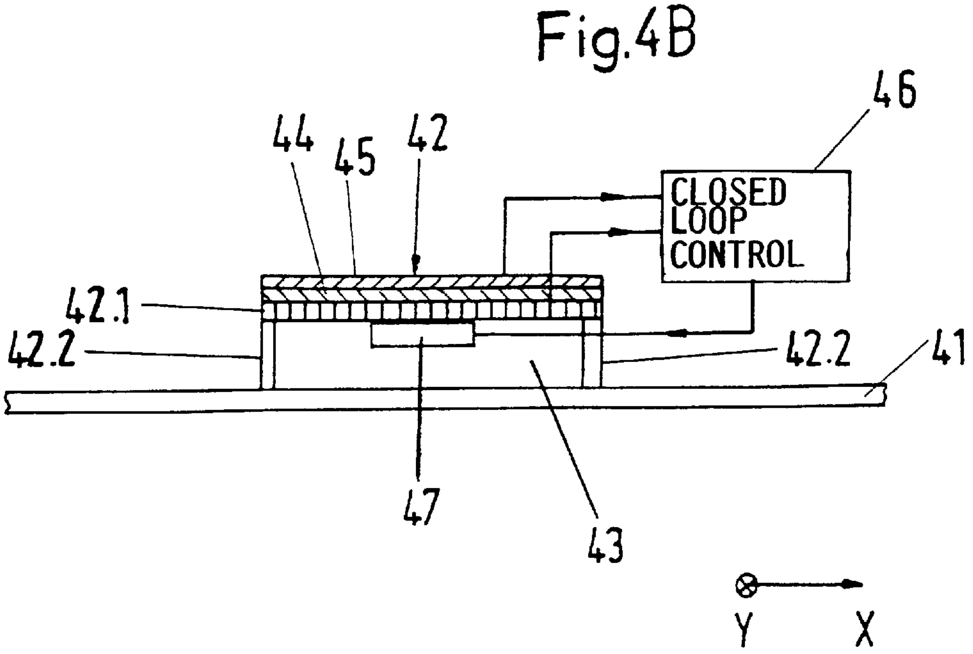
FIG. 4B is a sectional view through a noise suppressing box element of FIG. 4A and showing the arrangement of the sensors, the actuator and the feed-back control.

FIGS. 4A and 4B show an embodiment with sensor boxes 42 secured for example by an adhesive to a noise generating plate 41. Each sensor box 42 is provided with sensors in any of the forms disclosed above with reference to FIGS. 1, 2 or 3. It is preferred that the sensor boxes 42 cover as much surface area of the plate 41 as possible. As shown in FIG. 4B each sensor box 42 comprises a hard top shell 42.1 and side walls 42.2 spacing the hard top shell 42.1 from the surface of the plate 41 to which the sidewalls 42.2 are secured, for example by an adhesive. The top shell 42.1 and the side walls 42.2 enclose a hollow space 43 above the plate 41. The top shell 42.1 carries, as in the other embodiments, axially selective integrating sensors 44, 45, such as velocity sensors, acceleration sensors or deflection sensors. The output signals from these sensors 44, 45 are supplied to a closed loop control 46 which controls and excites an actuator 47 connected to the inner surface of the boxes, preferably centrally to the inner surface of each shell 42.1 for an active noise suppressing counteraction.

The embodiment shown in FIGS. 4A and 4B is especially suitable for noise suppression on noise generating structures having a complex noise radiating pattern which can be determined only with difficulties. The sensor boxes are actually excited by the vibration pattern of the plate structure 41, whereby even complex vibration patterns are sensed and processed for producing a respective control signal which then reduces or opposes the vibration pattern of the boxes and through the boxes the vibration of the plate structure 41 through the actuator 47.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. An apparatus for actively suppressing noise radiated by a component having a surface, said apparatus comprising at least a first sensor and a second sensor secured to said surface for producing noise representing control signals, an actuator (6, 47) connected to said surface (1, 21, 31, 42.1) for suppressing said noise in response to said control signal generated by said first and second sensors, wherein said first sensor has a first axially selective directional sensitivity effective in an x-direction for integrating vibrations in said x-direction to produce an x-direction sum signal (Sx) representing noise causing vibration components, and wherein said second sensor has a second axially selective directional sensitivity effective in a y-direction for simultaneously integrating vibrations in said y-direction to produce a y-direction sum signal (Sy) representing noise causing vibration components, whereby each first and second sensor integrates said vibrations in its own axial direction (x, y), wherein said first and second directional sensitivities extend orthogonally relative to each other, and wherein said at least first and second sensors are arranged with their respective axially selective directional sensitivities for sensing a vibration base mode and other vibration modes of said radiating component, said other vibration modes having uneven, odd numbers.

2. The apparatus of claim 1, wherein said at least first and second sensors are velocity sensors.

3. The apparatus of claim 1, wherein each of said at least first and second sensors comprises at least one strip shaped piezo-element that is sensitive in a longitudinal strip direction.

4. The apparatus of claim 3, wherein each of said at least first and second sensors comprises a plurality of piezo-strip elements that are arranged in parallel to each other and are connected electrically in parallel to each other.

5. The apparatus of claim 1, wherein each of said at least first and second sensors comprises a plurality of sensor elements (32) secured to said surface (31), wherein one set of sensor elements forms rows (32A) and another set of sensor elements forms columns (32B) crossing said rows to form a sensor matrix pattern on said surface, and wherein sensor elements of at least one row and sensor elements of at least one column are respectively electrically interconnected to form said sum signals (Sx and Sy).

6. The apparatus of claim 1, further comprising a hard shell (42.1), wherein said at least first and second sensors and said actuator are secured to said hard shell having side walls (42.2) enclosing a hollow space (43) on said noise radiating surface (41), and wherein said side walls (42.2) are connected to said noise radiating surface (41).

7. The apparatus of claim 6, comprising a plurality of said hard shells (42.1) arranged next to each other to form a surface covering pattern on said noise radiating surface.

8. The apparatus of claim 1, wherein said axially selectively sensitive sensors are selected from the group of velocity sensors, acceleration sensors, and displacement pick-ups.

9. The apparatus of claim 1, wherein each of said at least first and second sensors comprises at least one piezo-sensor film (3, 4).

10. The apparatus of claim 9, wherein said piezo-sensor films have a unidirectional piezoelectric characteristic.

11. The apparatus of claim 9, wherein said piezo-sensor films are made of stretched polyvinylidene fluoride.

12. The apparatus of claim 1, wherein said other uneven number vibration modes are effective in any one of said x-direction and in said y-direction.

13. The apparatus of claim 1, wherein each of said first and second sensors comprises a plurality of point sensors (32) arranged in rows (32A) and columns (32B) forming a matrix arrangement, and wherein said rows are sensitive in said x-direction and said columns are sensitive in said y-direction.

14. The apparatus of claim 13, wherein said rows are spaced from each other by a spacing (d), wherein said columns are also spaced from each other by said spacing (d), and wherein said spacing (d) is smaller than one quarter of a wavelength (β) of the highest vibration mode of said noise radiating component.

15. An apparatus for actively suppressing noise radiated by a component having a surface, said apparatus comprising at least a first sensor and a second sensor secured to said surface for producing noise representing control signals, an actuator (6, 47) connected to said surface (1, 21, 31, 42.1) for suppressing said noise in response to said control signal generated by said first and second sensors, wherein said first sensor has a first axially selective directional sensitivity effective in an x-direction for integrating vibrations in said x-direction to produce an x-direction sum signal (Sx) representing noise causing vibration components, and wherein said second sensor has a second axially selective directional sensitivity effective in a y-direction for simultaneously integrating vibrations in said y-direction to produce a y-direction sum signal (Sy) representing noise causing vibration components, whereby each first and second sensor integrates said vibrations in its own axial direction (x, y), wherein said first and second directional sensitivities extend orthogonally relative to each other, and wherein said at least first and second sensors are arranged with their respective axially selective directional sensitivities for sensing a vibration base mode and other vibration modes of said radiating component, wherein each of said first and second sensors comprises a plurality of point sensors (32) arranged in rows (32A) and columns (32B) forming a matrix arrangement, wherein said rows are sensitive in said x-direction and said columns are sensitive in said y-direction, wherein said rows are spaced from each other by a spacing (d), wherein said columns are also spaced from each other by said spacing (d), and wherein said spacing (d) is smaller than one quarter of a wavelength (β) of the highest vibration mode of said noise radiating component.

* * * * *